United States Patent [19]

Shoesmith, deceased

[11] Patent Number: Plant 5,970

[45] Date of Patent: May 5, 1987

[54] CHRYSANTHEMUM PLANT NAMED CHIPPER

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 712,692

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Chipper having a dwarf habit, free breaking, spoon ray florets, eight week response, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Chipper.

Chipper is a product of a planned breeding program which had the objective of creating new Chrysanthemum cultivars with eight (8) week response, bronze color, spoon-tipped form, and dwarf habit suitable for 9 cm. pots. Such traits in combination were not present in previously available commercial cultivars.

Chipper was originated from a hybridization made by Leonard H. Shoesmith in a controlled breeding program in Westfield, Woking, England in 1977. The male and female parents are unknown at this time. Chipper was discovered and selected as one flowering plant within the progeny of the parentage by applicant in November, 1978 in a controlled environment in West Chicago, Ill., and given the code name F8-373-YS.

The first act of asexual reproduction of Chipper was accomplished when vegetative cuttings were taken from the initial selection in February, 1979 in a controlled environment in West Chicago, Ill. by a technician working under formulations established and supervised by Leonard H. Shoesmith. Horticultural examination of selected units initiated in March, 1979 has demonstrated that the combination of characteristics as herein disclosed for Chipper are firmly fixed and are retained through successive generations of asexual reproduction.

Chipper has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Chipper, which in combination distinguish this Chrysanthemum as a new and distinct cultivar:

1. Dwarf habit.
2. Eight (8) week response.
3. Free breaking, (5–10 breaks).
4. Spoon ray florets.
5. Ability to be grown year around in 9 cm. pots in more areas, and requiring few B-9 treatments.

Of the many commercial cultivars known to the present inventor, the most similar in comparison to Chipper is the unpatented cultivar Starlet. In comparison to Starlet, Chipper has a more yellow flower color and has smaller diameter flowers. Chipper is not recommended as a garden mum in the north. The flower form and plant habit of Chipper when grown in 9 cm. pots are similar to those same characteristics of Starlet.

The accompanying photographic drawing shows typical inflorescense characteristics of Chipper, with colors being as nearly true as possible with illustrations of this type. The photograph is in black and white, with a single flower being colored to accurately depict true flower color.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., cv Chipper.

*Commercial.*—Daisy spray, four (4) inch pot.

I. INFLORESCENCE

A. Capitulum:

*Form.*—Flat.

*Type.*—Spoon daisy.

*Diameter across face.*—3–5 cm.

B. Corolla of ray florets:

*Color (general tonality from a distance of three meters).*—Bright yellow.

*Color (under surface).*—9 C.

*Color (top surface).*—9 B.

C. Corolla of disc florets:

*Color (mature).*—Yellow.

*Color (immature).*—Lime green.

D. Reproductive organs:

*Androecium.*—Present in disc florets only; numerous.

*Gynoecium.*—Present in both ray and disc florets; numerous.

II PLANT

A. General appearance:

*Height.*—10–15 cm. above edge of pot when properly grown in 9 cm. pot.

B. Foliage:

*Color* (*under surface*).—147 B.
*Color* (*top surface*).—147 A.
*Shape.*—Ovate and deeply lobed.

It is claimed:

1. A new and distinct cultivar of Chryanthemum named Chipper, as described and illustrated, and particularly characterized by its dwarf habit; free breaking; spoon ray florets; eight week response, and by its ability to be grown year around in 9 cm. pots with little growth regulation.

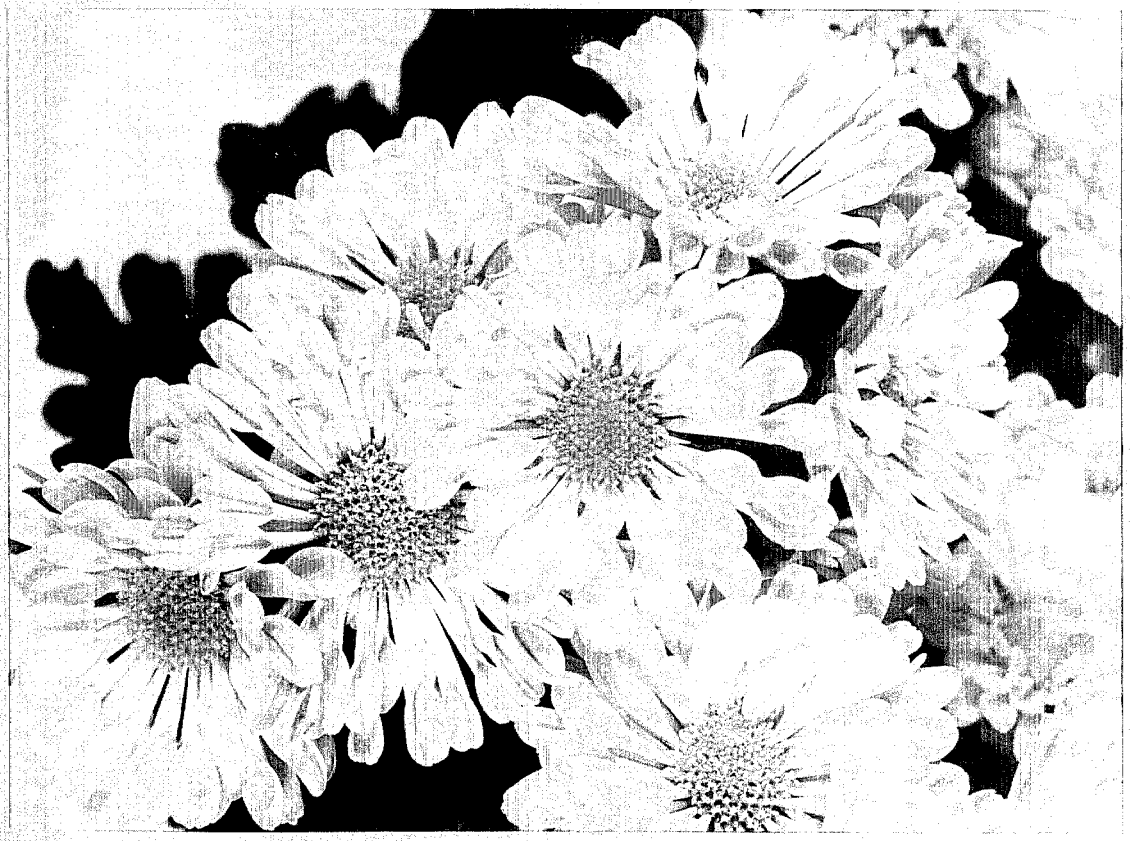

* * * * *